United States Patent [19]
Govindan et al.

[11] Patent Number: 6,010,680
[45] Date of Patent: *Jan. 4, 2000

[54] THIOLATION OF PROTEINS FOR RADIONUCLIDE-BASED RADIOIMMUNODETECTION AND RADIOIMMUNOTHERAPY

[75] Inventors: Seregulam V. Govindan, Summit; Ruth Grebenau, West Orange; Gary L. Griffiths, Morristown; Hans J. Hansen, Mystic Island, all of N.J.

[73] Assignee: Immunomedics, Inc., Morris Plains, N.J.

[ * ] Notice: This patent is subject to a terminal disclaimer.

[21] Appl. No.: 09/106,140

[22] Filed: Jun. 29, 1998

Related U.S. Application Data

[63] Continuation of application No. 08/779,556, Jan. 8, 1997, Pat. No. 5,772,981, which is a continuation of application No. 08/253,772, Jun. 3, 1994, abandoned.

[51] Int. Cl.$^7$ ............................ A61K 51/00; A61M 36/14
[52] U.S. Cl. ...................... 424/1.69; 424/1.11; 424/1.65; 424/9.1; 424/1.49; 424/130.1; 530/387.1
[58] Field of Search ................................ 424/130.1, 1.11, 424/1.49, 1.65, 1.69, 1.73, 9.1, 9.3, 9.4, 9.5, 9.6, 9.7; 530/300, 333, 334, 338, 331, 387.1, 387.2; 436/547, 548; 534/7, 10–16

[56] References Cited

U.S. PATENT DOCUMENTS

| | | |
|---|---|---|
| 3,198,781 | 8/1965 | Benesch et al. . |
| 4,323,546 | 4/1982 | Crockford et al. . |
| 4,424,200 | 1/1984 | Crockford et al. . |
| 4,883,842 | 11/1989 | Chervu et al. . |
| 4,980,147 | 12/1990 | Fritzberg et al. . |
| 5,061,641 | 10/1991 | Shochat . |
| 5,071,636 | 12/1991 | Yamauchi et al. . |
| 5,080,884 | 1/1992 | McBride et al. . |
| 5,082,930 | 1/1992 | Nicolotti et al. . |
| 5,102,990 | 4/1992 | Rhodes . |
| 5,128,119 | 7/1992 | Griffiths . |
| 5,162,505 | 11/1992 | Dean et al. . |
| 5,180,816 | 1/1993 | Dean . |
| 5,196,515 | 3/1993 | Levar et al. . |
| 5,225,180 | 7/1993 | Dean et al. . |
| 5,310,536 | 5/1994 | Srinivasan . |
| 5,426,190 | 6/1995 | Govindan et al. . |
| 5,443,815 | 8/1995 | Dean et al. . |
| 5,493,031 | 2/1996 | Govindan . |
| 5,496,533 | 3/1996 | Jackson et al. . |
| 5,508,020 | 4/1996 | Dean et al. . |
| 5,534,497 | 7/1996 | Verbruggen et al. . |
| 5,772,981 | 6/1998 | Govindan et al. ..................... 424/1.49 |

FOREIGN PATENT DOCUMENTS

| | | |
|---|---|---|
| 92/19274 | 11/1992 | WIPO . |
| 93/10747 | 6/1993 | WIPO . |
| 93/23085 | 11/1993 | WIPO . |

OTHER PUBLICATIONS

Greenfield, et al., Bioconjugate Chem., 1: 400–410 (1990)"Thiol–Containing Cross–Linking Agent with Enhanced Steric Hinderance".

*McGraw–Hill Dictionary of Chemical Terms*, Ed. Sybil Parker, 1984.

Khaw et al—J. Nucl. Med., 23:1011–19 (1982), "Technetium–99m Labeling of Antibodies to Cardiac Myosin Fab and to Human Fibrinogen."

Khaw, et al.—Science, 209:295–97 (1980), "Myocardial infarct Imaging of Antibodies to Canine Cardiac Myosin with Indium–111–Diethylenetriamine Pentaacetic Acid."

Krejcarek, et al.—Biochem. Byophys. Res. Commun., 77:581–85 (1977), "Covalent Attachment of Chelating Groups to Macromolecules."

Childs, et al.—J. Nucl. Med., 26:293 (1985), "Optimum Conditons for Labeling of DTPA Coupled Antibodies with Technetium–99m."

Fritzberg et al.—J. Nucl. Med., 27:957 (1986), "Radiopharmaceutical Chemistry v. Antibodies."

Baidoo et al. Cancer Research (Supp.) 50:799s–803s(1990), "Tc Labeling of Protein: Initial Evaluation of a Novel Diaminedithiol Bifunctional Chelating Agent."

Wong–Chemistry of Protein Conjugation and Cross–Linking, CRC Press, Inc., Boca Raton, Florida, pp. 17–23 (1991), "Reactive Groups of Proteins and Their Modifying Agents."

McCall et al.—Bioconjugate Chem. 1:222–26 (1990), "Simplified Method for Conjugating Macrocyclic Bifunctional Chelating Agents to Antibodies via 2–Iminothiolane."

Goff et al. Bioconjugate Chem. 1:381–86(1990), "Substituted 2–Iminothiolanes: Reagents for the Preparation of Disulfide Cross–Linked Congjugagtes with Increased Stability."

*Primary Examiner*—Shelley A. Dodson
*Assistant Examiner*—Dameron Jones
*Attorney, Agent, or Firm*—Foley & Lardner

[57] ABSTRACT

A method of radiolabeling a protein with a radionuclide including contacting the protein with a protected tertiary thiol-containing bifunctional chelating agent that is capable of reacting with the protein at one end of the agent and is capable of complexing with a radionuclide at the other end of the agent, to form a protein-acetyl-t-thiol-containing conjugate. The protein-acetyl-t-thiol-containing conjugate then is deprotected and admixed with a reducing agent for the radionuclide, where the radionuclide is added in a subsequent step, to form a mixture of reducing agent and protein-t-thiol-containing conjugate. This mixture then is reacted with a radionuclide whereby the radionuclide reacts with pendant sulfhydryl groups present on the protein-t-thiol-containing conjugate. Methods of radioimmunotherapy and diagnostic kits suitable for forming a composition to be administered to a human patient also are disclosed.

19 Claims, No Drawings

THIOLATION OF PROTEINS FOR RADIONUCLIDE-BASED RADIOIMMUNODETECTION AND RADIOIMMUNOTHERAPY

This application is a continuation of application Ser. No. 08/779,556, filed Jan. 8, 1997, now U.S. Pat. No. 5,772,981, which is in turn a continuation of Ser. No. 08/253,772, filed Jun. 3, 1994, now abandoned.

BACKGROUND OF THE INVENTION

1. Field of the Invention

This invention relates to one-vial methods and kits for radiolabeling a protein with a radiometal ion of a radionuclide that binds tightly to sulfhydryl groups by generating sulfhydryl groups on the protein using a tertiary thiol-containing chelating agent. Use of a tertiary thiol-containing chelating agent provides a protein containing a t-thiol-containing derivative that can be deprotected to generate free sulfhydryl groups which then are labeled with a radionuclide.

2. Description of Related Art

It is known that certain radiometals bind tightly to sulfur ligands, including, e.g., Tc-99m from reduced pertechnetate, Re-186 and Re-188 ions, Cu-67 ions, Hg-197 ions and Bi-212 ions. Some of these radiometals have been bound to proteins, especially antibodies or antibody fragments. Technetium-99m is an ideal radionuclide for scintigraphic imaging because of its nuclear properties. Technetium-99m has a single photon energy of 140 KeV, a half-life of about 6 hours and it is readily available from a $^{99}$Mo-$^{99m}$TC-generator.

The element below technetium in the periodic table, rhenium, has similar chemical properties and can be labeled to protein using similar techniques. There are some 34 isotopes of rhenium and two of them in particular, rhenium-186 ($t_{1/2}$ 90 hours, gamma 137 KeV, beta 1.07, 0.93 MeV) and rhenium-188 ($t_{1/2}$ 17 hours, gamma 155 KeV, beta 2.12 MeV) are prime candidates for radioimmunotherapy using monoclonal antibody approaches.

Two methods commonly are used to label proteins such as antibodies or antibody fragments with radiometals. The first approach is the direct labeling method whereby the radiometal is bound directly to the protein molecule. Direct labeling involves reducing the protein to generate free sulfhydryl groups and then directly attaching a reduced radionuclide to the free sulfhydryl groups. Direct labeling of protein has been accomplished using a "pre-tinning" protocol, requiring severe conditions and long "pre-tinning" times, but radiolabeling at 100% incorporation was not achieved; Crockford et al., U.S. Pat. No. 4,323,546 (see also U.S. Pat. No. 4,424,200). In this process, the presence of extremely high amounts of stannous ion for long periods compromised the immunoreactivity of the antibody. The process also generally necessitated a post-labeling purification column. Other direct labeling methods have required separate vials, one for antibody and one for stannous ion complexed to a transchelator such as a phosphate and/or phosphonate.

Another problem associated with the direct labeling method is that antibodies directly labeled with $^{99m}$Tc and/or Rhenium have been reported to be unstable in vivo, i.e., a significant proportion of the radionuclide dissociates from the labeled antibody fairly quickly upon injection of the labeled antibody into the bloodstream. When labeled antibody is used for external imaging, this instability leads to accumulation of radioactivity in locations other than those at which the radiolabeled antibody localize. This reduces the resolution of the method by attenuating the localized radioactivity and by increasing the background activity due to non-specific distribution of the radioisotope. Rhodes et al., TUMOR IMAGING, Chpt 12, pps 111–24 (Mason Publ., USA, 1982), disclose that unstable antibodies directly labeled with $^{99m}$Tc could be purified using an elaborate permeation chromatographic method which also complicates the method of directly radiolabeling proteins. Finally, the presence of residual technetium is difficult to remove as are the colloids it may form, and both tend to contribute to undesirable non-specific background radiation.

The second method of radiolabeling proteins is the indirect method whereby a complexing agent is coupled to the protein and the radiometal is attached to the protein via the complexing agent. The complexing agent typically contains free or protected sulfhydryl groups that are capable of complexing with the reduced radionuclide on one end and groups capable of reacting with the protein on the other end. Indirect labeling methods using conjugated chelating groups such as diethylenetriaminepentaacetic acid (DTPA) (Khaw et al., *J. Nucl. Med.*, 23:1011–19 (1982) or a variety of sulfur/nitrogen ($S_2N_2$) chelators such as bis-thiosemicarbozones and the like are known. Khaw et al., *Science*, 209:295–97 (1980) discloses antibodies to cardiac myosin labeled with indium-111 via DTPA and use of the labeled antibodies to image for myocardial infarction. See also, Krejcarek et al., *Biochem. Byophys. Res. Commun.*, 77:581–85 (1977); Childs, R. L. and Hnatowich, D. J., *J. Nucl. Med.*, 26:293 (1985). In a more recent approach, Fritzberg et al. *J. Nucl. Med.*, 27:957 (1986), Baidoo et al., *Cancer Research (Suppl.)*, 50:799s-803s, (1990) describe the use of a particular diamidodithiol and diaminodithiol groups as chelating agents.

These chelating agents include free thiol groups that may serve to reduce disulfide bonds in the protein to be labeled. Thus, labeling in accordance with the methods described in the aforementioned documents can occur either directly at the reduced disulfide bonds in the protein or on the free sulfhydryl groups on the chelating agents. These methods also typically include the use of a transchelator such as glucoheptonate to keep the reducing agent in solution. The methods disclosed in Fritzberg et al. and Baidoo et al. therefore are not practical and easy to use, and may not specifically label the chelating agent on the pendant free sulfhydryl groups of the chelating agent.

Many of the aforementioned conventional chelate-based indirect labeling techniques often involve elaborate syntheses of chelating agents, and, frequently, the need for a 'pre-labeling' procedure to accomplish antibody radiolabeling. These processing steps compromise the certain qualities such as ease of use, and practicality typically desired in the diagnostic industry. Other indirect labeling methods involve the thiolation of proteins; Wong, S. S., in CHEMISTRY OF PROTEIN CONJUGATION AND CROSS-LINKING, CRC Press, Inc., Boca Raton, Fla., pp 17–23 (1991). Methods using ring-opening of iminothiolane such as those described in McCall, M. J., Diril H., and Meares, C. F., *Bioconjugate Cem.* 1:222–26, (1990) and Goff, D. A. and Carroll, S. F., *Bioconjugate Chem.* 1:381–86 (1990), have the disadvantage of continually generating thiols, resulting in the formation of aggregates, thus necessitating simultaneous derivatization of generated thiols. The use of N-acetylhomocysteine thiolactone also is expected to result in similar problems. S-acetylmercaptosuccinic anhydride is often employed as a thiolating agent, in a reaction with lysine residues of proteins, with the thiol acetate converted to thiol in a subsequent step. Use of this reagent, however, results in an alteration of the overall charge ratio of the thiolated protein, which has implications for the conformation and pharmacokinetics of the antibody, Wong et al., supra. Other reagents, such as (3-acetylthio propionyl)-thiazolidine-2-thione, will generate, after deprotection, a mercapto group which is attached to an unsubstituted methylene group.

Dean, U.S. Pat. No. 5,180,816 discloses a method of radiolabeling an antibody with technetium whereby a chelating agent containing a primary thiol group is used to attach to free sulfhydryl groups on the antibody. Hence, the antibody first is reduced and cleaved to fragments to generate free sulfhydryl groups, or alternatively, the protein is thiolated with, for example, 2-iminothiolane to generate free sulfhydryl groups. A chelating agent containing a protected thiol group at one end then is used to attach to the free sulfhydryl groups on the antibody at the other end, and is subsequently deprotected and contacted with technetium to effect radiolabeling. The process of Dean involves a disadvantageous cleavage of the antibody which may result in excessive fragmentation or destruction of the antigen binding site on the antibody.

Indirect labeling of a protein without generation of free sulfhydryl groups, i.e., by attachment of the chelating agent to, for example, amino functionalities on the protein, is not possible with Dean's primary thiol-containing chelating agents even though Dean mentions that a N-hydroxysuccinimide ester may be used to bind the chelating agent to the amine functions on the protein. The reason for this is that the protein amino groups react not only with the N-hydroxysuccinimide carboxylic esters, but they also cleave the protected primary thiol group at the opposite end of the chelating agent. This cleavage results in premature deprotection and oxidation of the generated free thiol groups and prevents efficient and quantitative labeling of the antibody.

Other problems associated with the use of chelating agents is that one-pot labeling where the protein-chelating agent conjugate is contacted with tin prior to reaction with the radionuclide is not possible. The reason for this is because the presence of the tin reduces the disulfide bonds in the protein thereby destroying the chelator-specificity of the radiolabel and possibly destroying the efficacy of the protein. In addition, many chelating agents when used in immunotherapy using rhenium as the radionuclide often accumulate in toxic amounts in the kidney. For imaging purposes, many radiolabeled proteins, for example, whole IgG, radiolabeled with technetium, tends to clear to and congregate in the liver thereby adversely affecting the efficiency of the imaging since many tumors can be metastasized throughout the body. Also, the tumor to non-tumor ratio for many conventional radiolabeled proteins tends to be too low thereby adsversely affecting the efficiency of the image.

Thus, there exists a need to develop a method of labeling a protein using a chelating agent that is capable of forming a complex with a non-antigenic binding site on a protein that has not been reduced or thiolated, and that is capable of forming a complex with a radionuclide so that the radiolabeled protein is not further cleaved when contacted with tin and subsequently frozen or lyophilized. There also exists a need to develop a method of labeling a protein by using a bifunctional chelating agent containing pendant protected thiol groups whereby the reactive groups on the protein will not prematurely cleave the protected thiol groups on the bifunctional chelating agent. There also exists a need to develop a method and kit that is easy to use and does not involve complicated synthesis procedures or multiple containers for the protein and reducing agent and does not involve the use of a transchelator. There also exists a need to develop a method of radiolabeling a protein for use in radioimmunoimaging or radioimmunotherapy whereby the radiolabeled protein has good tumor uptake, low kidney uptake, does not clear entirely in the liver, spreads out broadly throughout the body and provides a good tumor to non-tumor ratio for imaging purposes. There also exists a need to develop a method of radiolabeling a F(ab')$_2$ monoclonal antibody that does not subsequently cleave to Fab' even if tin is present in the one-pot labeling kit.

SUMMARY OF THE INVENTION

It is an object of the present invention to provide a method and kit useful for indirectly radiolabeling a protein with a radionuclide using a chelating agent that is easy to synthesize and a method that does not involve complicated reducing procedures including the use of excess reducing agent. It also is an object of the present invention to provide a one-vial method and kit for indirectly radiolabeling a protein that is capable of being used by a clinician or technician prior to the use of the labeled protein, and that does not result in premature cleavage of the protein during incubation with the reducing agent for the radionuclide. An additional object of the present invention is to provide a method and kit for indirectly radiolabeling a protein whereby the radionuclide is complexed with the chelating agent. An additional object of the present invention is to provide a method and kit for indirectly radiolabeling a protein for use in radioimmunoimaging or radioimmunotherapy whereby the radiolabeled protein has good tumor uptake, low kidney uptake, does not clear entirely in the liver, spreads out broadly throughout the body and provides a good tumor to non-tumor ratio for imaging purposes.

In accordance with these and other objects of the present invention, there is provided a method for indirectly labeling a protein comprising (a) contacting a tertiary thiol-containing chelating agent that is capable of reacting with the protein at one end of the agent without cleaving disulfide bonds of the protein, and that is capable of complexing with a radionuclide at the other end of the chelating agent, with a protein to produce a protein-acetyl-t-thiol-containing derivative, (b) deprotecting the acetyl-t-thiol group to produce a free sulfhydryl group, (c) admixing the deprotected protein-chelating agent conjugate with a reducing agent for a radionuclide, the radionuclide to be added in a subsequent step; and (d) contacting the resultant mixture of step (c) with a reducible radionuclide. The reduced radionuclide reacts with the pendant free sulfhydryl group present on the deprotected protein-chelating agent conjugate. Preferably, the radionuclide reacts with the pendant free sulfhydryl group to form a five- or six-membered ring.

In accordance with an additional object of the present invention, there is provided a method for indirectly labeling a protein comprising contacting, in a single vial, (A) a mixture comprised of (i) a reducing agent for a reducible radionuclide, and (ii) a t-thiol-containing derivative prepared in accordance with the method described above (steps (a) and (b)), with (B) a radionuclide in unreduced form.

In accordance with an additional object of the present invention, there is provided a kit for indirectly labeling a protein comprising a single vial containing a mixture comprising (i) a reducing agent for a reducible radionuclide, the radionuclide to be added in a subsequent step, and (ii) a t-thiol-containing derivative of a protein molecule prepared in accordance with the above-described method (steps (a) and (b)), either frozen or in lyophilized form.

In accordance with another embodiment of the present invention, there is provided a method of radioimmunoimaging a tumor, an infectious lesion, a myocardial infarction, a clot, atherosclerotic plaque, or a normal organ or tissue, wherein a protein, an antibody or antibody fragment that specifically binds to an antigen produced by or associated with the tumor, etc;, and radiolabeled with a pharmaceutically inert radioisotope capable of external detection, is parenterally injected into a human patient and, after a sufficient time for the radiolabeled antibody or antibody fragment to localize and for non-target background to clear, the site or sites of accretion of the radiolabeled protein, antibody or antibody fragment are detected by an external imaging camera, it will be an improvement to use as the radiolabeled protein, antibody or antibody fragment a labeled protein, antibody or antibody fragment made according to the method of the present invention. The radiolabled proteins made in accordance with the claimed method, when used in such radioimmunoimaging methods, so not suffer from the aforementioned disadvantages with respect to clearance to the liver and target-to-non-target ratio, etc.

In accordance with another embodiment of the present invention, there is provided a method of radioimmunotherapy including the steps of (a) contacting a protein that specifically binds to an antigen produced by or associated with a tumor or an infectious lesion, with a tertiary thiol-containing bifunctional chelating agent that is capable of reacting with the protein at one end of the agent without cleaving disulfide bonds on the protein, and that is capable of complexing with a radionuclide at the other end of the agent, to form a protein-acetyl-t-thiol-containing conjugate. The protein-acetyl-t-thiol-containing conjugate then is deprotected and admixed with a reducing agent for a therapeutically effective reducible radionuclide, where the reducible radionuclide is to be added in a subsequent step, to form a mixture of reducing agent and protein-t-thiol-containing conjugate. This mixture then is reacted with a therapeutically effective reducible radionuclide whereby the radionuclide reacts with pendant sulfhydryl groups present on the protein-t-thiol-containing conjugate to produce a solution containing a radiolabeled protein-t-thiol-containing conjugate which in turn is parenterally administered to a patient suffering from a tumor or infectious lesion. Such a radiolabeled protein does not suffer from the disadvantages discussed above with respect to excessive kidney uptake and the like.

DETAILED DESCRIPTION

The present inventors have found that a protein, e.g., an antibody or antibody fragment, having pendant sulfhydryl groups by virtue of the use of a chelating agent containing protected pendant thiol groups which are subsequently deprotected to generate free sulfhydryl groups, can selectively bind radiometal ions to form tight bonds to the sulfhydryl groups. These radiolabeled proteins are very effective when used in radioimmunoimaging and radioimmunotherapeutic methods due to their ability to attach to tumor, avoid excessive kidney uptake, avoid excessive clearance to the liver and provide good tumor to non-tumor ratios. In addition, the method of radiolabeling enables one-pot labeling of a protein that has not been reduced, i.e., $F(ab')_2$, whereby the protein is conjugated with a chelating agent and then contacted with a reducing agent for the radionuclide in such a manner that the reducing agent does not cleave the protein, i.e., $F(ab')_2$ to Fab'. The present inventors further have found that a protein can be labeled in the above manner without the need to reduce the protein thereby running the risk of cleaving too many disulfide bonds or altering the binding specificity of the protein. In addition, the present inventors have found that the use of a tertiary thiol containing chelating agent allows attachment to a protein without generating free sulfhydryl groups on the protein or reducing the protein, and without cleavage of the protected thiol groups on the chelating agent thereby preventing premature deprotection and oxidative loss of free thiol groups. Both the reagents and the conditions in the present method are greatly simplified, and the method is particularly suitable for technetium or rhenium labeling either utilizing a transchelator such as glucoheptonate or by using tin as a reducing agent in a one-vial kit.

Throughout this description; the term "protein" denotes a polypeptide having two or more amino acids. Advantageously, "protein" denotes a whole antibody (i.e., IgG), and antibody fragments such as $F(ab')_2$, Fab' or Fab. These whole antibodies or antibody fragments contain both stable and non-stable labeling sites for reduced technetium or rhenium ions. The "non-stable site" (which may be one or more sites) has a high capacity but a low affinity for reduced technetium (it is understood hereinafter that rhenium ions are included when the more commonly used technetium ions are discussed, since the chemistry of technetium and rhenium is substantially the same for labeling purposes, although binding constants may be somewhat different). This non-stable site accounts for about 85% of the total direct labeling of $F(ab')_2$ fragments and 76% of the total labeling of IgG with reduced $^{99m}Tc$. The second site gives rise to a stable label and accounts for 15% and 24% of the total labeling of $F(ab')_2$ and IgG with $^{99m}Tc$, respectively.

The present inventors, while not intending to be bound by any theory, believe that indirect labeling of protein using a protected tertiary thiol-containing chelating agent to generate an acetyl-t-thiol-containing protein derivative enables attachment to specific non-antigenic binding sites on an antibody without premature cleavage of the protected thiol at the other end of the tertiary thiol-containing chelating agent and without cleavage of disulfide bonds on the protein. In addition, the present inventors have found that the disulfide bonds of the protein in protein-chelating agent conjugates of the present invention, when admixed with a reducing agent for a radionuclide in a one-vial kit, are not cleaved to produce smaller fragments that may not have the requisite binding specificity or antigenicity or to produce pendant sulfhydryl groups on the protein. Hence, the use of the t-thiol-containing chelating agents of the present invention enables labeling specifically on the deprotected chelating agent's pendant sulfhydryl groups and not on any free sulfhydryl groups present on the protein. While not intending to be bound by any theory, the present inventors believe that the protected tertiary thiol-containing chelating agent has an enhanced resistance to acyl cleavage reactions thereby preventing the reactive functionalities on the protein, i.e., the amino functionalities, from prematurely deprotecting the thiol groups, and the use of the inventive chelating agents prevents inadvertent reduction of disulfide bonds in the protein. The present method further substantially avoids the undesirable formation of colloid during the course of the labeling process and, under appropriate proportions of reducing agent and exclusion of oxygen, the present method prevents the accumulation of residual pertechnetate as a contaminant.

It will be understood that the proteins including the antibodies or antibody fragments to be radiolabeled can be antibodies that bind to antigens which include but are not limited to antigens produced by or associated with tumors, infectious lesions, microorganisms, parasites, myocardial infarctions, clots, atherosclerotic plaque, or normal organs or tissues. Throughout this description, the terms "antibody" or "antibody fragment" denote generally immunoglobulins that specifically bind to antigens to form immune complexes. These terms include conventional IgG, IgA, IgE, IgM, and the like, conventional enzyme digestion products such as F(ab')$_2$ fragments obtained by pepsin digestion of intact immunoglobulins, Fab fragments obtained by papain digestion of intact immunoglobulins, conventional monovalent Fab' and light-heavy chain fragments obtained by disulfide bond cleavage of F(ab')$_2$ fragments and intact antibody, respectively, as well as products having substantially similar properties to such immunoglobulins and fragments. Such similar proteins include antibody sub-fragments made by further digestion or manipulation of larger fragments, genetically engineered antibodies and/or fragments, and synthetic proteins having an antigen recognition domain which specifically binds to an antigen in a substantially analogous fashion to a "classical" immunoglobulin. It will be understood that the fragments of the proteins need not and preferably should not contain free sulfhydryl groups.

The present method advantageously labels proteins such as whole antibodies (IgG) or antibody fragments F(ab')$_2$, Fab' or Fab, and more advantageously F(ab')$_2$ monoclonal antibody. Typical methods of direct or indirect labeling of F(ab')$_2$ usually involved reduction of a whole antibody to F(ab')$_2$. It has been found, however, that attempts to achieve partial reduction of F(ab')$_2$ resulting from enzymatic cleavage of intact antibody often result in considerable further cleavage to Fab', and that even later attempts to reduce pertechnetate or perrhenate with stannous ion, in the presence of F(ab')$_2$, are accompanied by disulfide bond reduction and further cleavage to Fab', resulting in some label being lost to the monovalent fragment, and possibly resulting in such excessive fragmentation of F(ab')$_2$ to destroy is efficacy. In addition, use of chelating agents that include free sulfhydryl groups has led to disulfide bond reduction and inadvertent cleavage resulting in some label being lost to the antibody or antibody fragment instead of reacting with the pendant free sulfhydryl groups on the chelating agent. For improved production of F(ab')$_2$ antibody conjugates with the bifunctional chelating agent, substantially free of further Fab' cleavage products, it has surprisingly and unexpectedly been found that reaction of F(ab')$_2$ and a protected tertiary thiol-containing chelating agent results in highly efficient labeling of the F(ab')$_2$.

The method of the present invention includes contacting the protein with a protected tertiary thiol-containing chelating agent to produce a protein-chelating agent conjugate that contains at least one tertiary protected thiol group. The tertiary thiol-containing chelating agent is covalently bound to the protein and serves to couple the protein and the radiometal after deprotection. Methods for effecting such covalent bonding are well known to those skilled in the art. For example, an active ester (e.g., N-hydroxysuccinimide ester) or an isothiocyanate derivative of the coupling agent may be used to bind the agent to amino functions on the protein; a 2-iodoacetyl or maleimido derivative of the coupling agent may be used to bind the agent to sulfhydryl groups of the protein; a hydrazide derivative of the agent may be used to bind the agent to oxidized carbohydrate groups on the protein; or a carbodiimide reagent such as 1-ethyl-3-(3-diaminopropyl)carbodiimide may be used to bind an amino group of the chelating agent to a carboxyl group on the protein. Whole antibodies (IgG) and peptides naturally occur with amine and carboxyl groups. Advantageously, the protected tertiary thiol-containing chelating agent of the present invention forms a complex with an amine functionality on the antibody, where the antibody has not been reduced or thiolated to generate free sulfhydryl groups. More advantageously, the protected tertiary thiol-containing chelating agent of the present invention forms a complex with an amine functionality on the protein and the amine functionality does not react with the protected thiol group on the chelating agent resulting in its premature deprotection to sulfhydryl.

The protected tertiary thiol-containing chelating agents useful in the present invention are any chelating agents containing an electrophilic or nucleophilic portion capable of forming a stable bond with a protein functionality, as described above, and a complexing portion containing at least one protected tertiary thiol group which portion is capable of complexing a desired radionuclide after deprotection, and that does not react with the protein functionality to prematurely deprotect the thiol group. Advantageously, the tertiary thiol-containing chelating agent forms a 5- or 6-membered ring complex with the desired radionuclide. More advantageously, the tertiary thiol-containing chelating agent of the present invention forms an acetyl-t-thiol-containing derivative which can be deprotected and labeled with technetium. Such chelating agents include, but are not limited to (N-hydroxysuccinimidyl)-N-(3-methyl-3-acylmercapto butyryl) glycinate and reaction products of this compound with diglycine or triglycine.

Since any pendant sulfhydryl groups present in the chelating agent may be incompatible with a sulfhydryl-selective electrophile which may be part of the same coupling agent, the sulfhydryl group may be suitably protected from reaction with the electrophilic moiety during attachment of the chelating agent. The protected thiol then can be deprotected using mechanisms well known to those skilled in the art. The phrase "protected thiol" as used herein denotes a thiol-containing moiety wherein the thiol group is reversibly derivatized such that the thiol is rendered unreactive. After attachment to the protein substrate, the chelating moiety can be deprotected to unmask the chelating functionality for radionuclide binding. In particular, the protected thiol is deprotected to generate pendant free sulfhydryl groups capable of complexing with the radionuclide.

Groups that are suitable for protecting the thiol from reaction are organic and inorganic groups which can readily be removed under mild conditions to regenerate the free sulfhydryl in the presence of the protein without substantially altering the activity of the protein. Advantageously, the thiol protecting group is a thiol ester. Those skilled in the art are familiar with the procedures of protecting and deprotecting thiol groups and to do so within the confines of the present invention is within the purview of the ordinarily skilled artisan.

The method of the present invention includes contacting a deprotected protein-chelating agent conjugate with a reducing agent for reducing a radionuclide, where the radionuclide is to be added later. The deprotected protein-chelating agent conjugate and the reducing agent typically are frozen or lyophilized thereby preventing cleavage of disulfide bonds in the protein due to the presence of the reducing agent. The present invention also encompasses a kit that includes a deprotected protein-chelating agent conjugate and a reducing agent for reducing a radionuclide, where the radionuclide is to be added subsequently. Upon addition of the reducing agent, the mixture can be used in performing the radiolabeling method of the present invention. A radionuclide can be added to the kit to provide a radiolabeled protein. In addition, if a protected protein-chelating agent conjugate is used, a deprotecting agent can be added before addition of the non-prereduced radionuclide. The single vials or kits of the present invention are designed to contain the appropriate protein, antibody, antibody fragment or the like, complexed with the tertiary thiol-containing chelating agent, for any particular immunodiagnostic or immunotherapeutic procedure.

In accordance with the present method, the vials or kits advantageously are sealed and provided with a mechanism of introducing or withdrawing reagents under sterile or semi-sterile conditions. Preferably, a vial containing a port for syringe injection is used in the present method. The reagents in the vials or kits typically are provided in aqueous, frozen or lyophilized form. In one embodiment the reagents can be stored at low temperature, e.g., in the refrigerator, for several days to several weeks, preferably at a pH of about 3.5–5.5, more preferably at pH 4.5–5.0, advantageously under an inert gas atmosphere, e.g., nitrogen or argon.

It also is within the scope of the present invention to provide the reagents in lyophilized form for ease of storage and stabilization. This is advantageously effected at pH of about 5.5, from a solution of a volatile buffer, e.g., ammonium acetate, and preferably also in the presence of a stabilizer to prevent aggregation, e.g., a sugar such as trehalose or sucrose. Such lyophilization conditions are conventional and well known to the ordinarily skilled artisan. The reagents also can be frozen and then thawed prior to use, but this procedure carries a greater risk of reoxidation and aggregation of the protein-chelating agent conjugate.

The labeling procedure of the present invention then can be performed simply by adding the radioisotope e.g., in the form of aqueous sodium pertechnetate, to the vial containing the reducing agent and the deprotected protein-chelating agent conjugate. In addition, if a protected protein-chelating agent conjugate is used, a deprotecting agent can be added before or during addition of the radioisotope to effect substantially 100% incorporation. The contents of the vial then are mixed and incubated for a time sufficient to effect labeling of the protein. The duration and condition of incubation are not crucial, but incubation typically is carried out for a period of time sufficient to obtain substantially 100% incorporation of $^{99m}$Tc to the protein. "Substantially 100% incorporation," as it pertains to technetium labeling, denotes greater than 98% incorporation, advantageously, greater than 99% and more advantageously 100% incorporation. Usually, the incubation is conducted for a period of time of from about 0.1 to about 60 minutes, and advantageously for a period of time of from about 1 to about 5 minutes. The radiolabeled protein then can be withdrawn from the vial, and immediately used since separation or purification is not required.

The reducing agent for the radionuclide advantageously is tin(II), preferably in the form of stannous ions. Typically, stannous chloride is added to the mixture containing the protein-chelating agent conjugate. It is understood by those skilled in the art that stannous ions can be generated in situ from tin metal, e.g., foil, granules, powder, turnings and the like, by contact with aqueous acid, e.g., HCl and is usually added in the form of $SnCl_2$, advantageously in a solution that is also about 0.1 mM in HCl.

In general, it is advantageous to work with a concentration of protein of about 0.01–10 mg per ml, preferably about 0.1–5 mg/ml, of solution, generally in saline, preferably buffered to a mildly acidic pH of about 4.0–4.5. In such case, the amount of stannous ion needed for reduction of a normal imaging activity of pertechnetate is about 0.1–50 $\mu$g/ml, preferably about 0.5–25 $\mu$g/ml, in proportion to the amount of protein. When labeling the foregoing quantity of protein, the amount of pertechnetate is generally about 2–50 mCi/mg of protein, and the time of reaction is about 0.1–30 minutes. With the preferred concentrations of protein and stannous ions, the amount of pertechnetate is preferably about 5–30 mCi/mg, and the time of reaction is preferably about 1–20 minutes.

Pertechnetate is generally obtained from a commercially available generator, most commonly in the form of $NaTcO_4$, normally in saline solution. Other forms of pertechnetate may be used, with appropriate modification of the procedure, as would be suggested by the supplier of a new form of generator or as would be apparent to the ordinarily skilled artisan.

Pertechnetate is generally used at an activity of about 0.2–10 mCi/ml in saline, e.g., 0.9% ("physiological") saline, buffered at a pH of about 3–7, preferably, 3.5–5.5, more preferably about 4.5–5.0. Suitable buffers include, e.g., acetate, tartrate, citrate, phosphate and the like. The reduction of pertechnetate normally is conducted under an inert gas atmosphere, e.g., nitrogen, argon or the like. The reaction temperature is generally maintained at about room temperature, e.g., 18°–25° C.

Throughout this description, the phrases "reduced pertechnetate" or "reduced perrhenate" denote the species of technetium or rhenium ion formed by stannous ion reduction of pertechnetate or perrhenate and chelated by the thiol group(s). It is generally thought that reduced pretechnetate is in the form of Tc(III) and/or Tc(IV) and/or Tc(V) in such chelates, and that reduced perrhenate is in the form of Re(III) and/or Re(IV) and/or Re(V), but higher or lower oxidation states and/or multiple oxidation states are included within the scope of the present invention.

Rhenium is found just below technetium in the periodic table, has the same outer shell electronic configuration and therefore is expected to have very similar chemical properties to technetium, especially its behavior with analogous compounds. In fact, rhenium compounds qualitatively behave similarly to technetium compounds insofar as reduction and chelation are concerned but their reaction rates are quite different and they are dissimilar in certain important respects. Despite these differences, the skilled artisan is capable of modifying the present invention based on the disclosure of technetium labeling to achieve efficient rhenium labeling (see, for example, Griffiths, U.S. Pat. No. 5,128,119, the disclosure of which is incorporated by reference herein in its entirety).

The radioisotope Re-186 is attractive for therapy and can also be used for imaging. It has a half-life of about 3.7 days, a high LET beta emission (1.07) MeV) and a convenient gamma emission energy (0.137 MeV). By analogy to technetium, rhenium is produced from perrhenate, and the reduced rhenium ions can bind non-specifically to protein. Accordingly, a method for Re-186 labeling of proteins, wherein the reduced perrhenate is bound to sulfhydryl groups on a protein-chelating agent complex, would be advantageous. Re-188 is a generator-produced beta and gamma emitter with a half-life of about 17 hours and is suitable for imaging and therapy. The development of commercial generators for rhenium-188 is currently underway; and in a preferred scenario, carrier free rhenium-188 is added directly to a vial containing stannous ions and a protein-chelating agent complex, to produce a rhenium radiolabeled protein which is ready for use in less than about two hours.

In general, the concentration of uncomplexed protein, e.g., antibody, the reaction times, perrhenate activities and other conditions will be substantially the same as for Re-186 or Re-188 labeling, except that a larger amount of stannous ion is used. When the radioisotope in the radioperrhenate is substantially carrier-free Re-188, the concentration of antibody or antibody fragment in the solution is advantageously about 1–20 mg/ml, preferably about 10–20 mg/ml and the amount of stannous ion is about 500–10,000 µg/ml, preferably about 500–5,000 µg/ml. When the radioisotope in the radioperrhenate is carrier-added Re-186, at the same concentration of antibody or antibody fragment, the amount of stannous ion is about 5–1,000 mg/ml, preferably about 50–500 mg/ml.

Copper ions also are tightly chelated by sulfur chelators. Cu-67 is another attractive radionuclide for imaging and therapy. It has a half-life of about 2.6 days, a beta emission (0.57 MeV) and a gamma emission (0.185 MeV), although the beta energy is relatively low. Cu-67 is relatively expensive and not readily available at present, although such conditions may change as demand develops. Cu-67 has the advantage that if forms tight chelates with thiols, the labeling is simple and rapid, and requires no reducing agent for the radiometal.

Other radionuclides with similar chelation behavior to copper, e.g., mercury, silver and lead, also could be bound to thiol-containing compounds according to the method of the present invention. Hg-197 has a half-life of about 1.5 days, and emits gamma radiation in an energy range of 78–268 KeV, and Pb-203 is a strong gamma-emitter at about 275 KeV, with a half-life of about 51 hours, making mercury and lead suitable for gamma scintigraphy. Ag-111 has a half-life of 7 days and emits beta radiation at about 1.02 MeV, and Bi-212 is an alpha-emitter with a half-life of about 1 hour and an energy of 6.09 MeV, making them of considerable interest for in vivo therapy. Bi-212 is produced in situ from a Pb-212 precursor with emission of gamma radiation of 239 KeV, with a half-life of about 10.6 hours. Thus, antibody-tertiary thiol-containing chelating agent conjugates for Bi-212 therapy will be Pb-212-labeled conjugates, and the short-hand notation lead/bismuth or Pb/Bi is used herein to indicate this. It will be understood that the invention is not limited to the exemplified radionuclide, but is generally applicable to ions that bind tightly to sulfhydryl groups.

The aforementioned labeling conditions typically result in substantially 100% incorporation, or substantially quantitative incorporation, of the label into the protein-chelating agent complex. Throughout this description, the phrase "substantial quantitative incorporation" as it pertains to rhenium labeling, denotes greater than about 80% incorporation, advantageously, greater than about 85% and more advantageously, greater than about 90% incorporation. For example, it now is possible to consistently label F(ab')$_2$, complexed with a tertiary thiol-containing chelating agent, with from 5 to 200 micrograms of Sn(II) per milligram of F(ab')$_2$, in essentially quantitative yield. Furthermore, the immunoreactivity of this labeled protein is hardly reduced after this serum incubation, showing that the radiolabeled protein-chelating agent conjugates are still completely viable imaging agents out to at least 24 hours.

At the aforementioned reaction conditions, for technetium labeling, no transchelator such as phosphonate, tartrate, glucoheptonate or other well known Sn(II) chelating agent is required to keep the tin in solution, however, such transchelators can be used in accordance with the present invention. Sn(II) compounds such as stannous chloride and stannous are preferred for use in the present method, although other readily available and conventional Sn(II) salts also are effective. There are only three essential ingredients; the deprotected protein-chelating agent conjugate, the aqueous stannous ion and the pertechnetate solution. Under the reaction conditions described herein, substantially 100% of Tc-99m incorporation into protein can readily be achieved.

The resultant radiolabeled protein is suitable for use in scintigraphic imaging of, e.g., tumors, infectious lesions, microorganisms, clots, myocardial infarctions, atherosclerotic plaque, or normal organs and tissues. Such imaging methods are well known in the art. The radiolabeled protein solutions as prepared above are ready for immediate injection, if done in a properly sterilized, pyrogen-free vial. Also, no blocking of free sulfhydryl groups after technetium binding is necessary for stabilization.

The method of the present invention is particularly attractive for labeling whole antibodies and antibody fragments, although proteins such as albumin, drugs, cytokines, enzymes, hormones, immune modulators, receptor proteins and the like may also be labeled. Antibodies contain one or more disulfide bonds which link the heavy chains, as well as disulfide bonds which join light and heavy chains together. Known methods that involve cleavage of these disulfide bonds typically set out to selectively cleave only the disulfide bonds linking the heavy chains and not the disulfide bonds that join the light and heavy chains together. Unfortunately, these methods sometimes, if not carried out with caution, can cause undesirable cleavage of the disulfide bonds that join the light and heavy chains together thereby rendering the antibody useless. In addition, use of chelating agents that have free thiol groups also can result in cleavage of disulfide bonds in the protein. The present method specifically avoids such undesirable cleavage by using the protected tertiary thiol-containing chelating agent and complexing it with a functional group on the whole antibody or antibody fragment, preferably an amine group thereby leaving the disulfide bonds intact.

The method of the present invention also encompasses the use of a water-soluble transfer ligand that complexes with the reduced radionuclide. In general, the transfer ligands useful in an alternative embodiment of the present invention are water soluble (or can be made water soluble) chelators which are capable of complexing technetium-99m or any of the rhenium radioisotopes in the reduced state or other known radioisotopes to form a stable metal ion/ligand complex. The complex is further capable of exchanging the radioisotope with the pendant sulfhydryl groups present on the protein-chelating agent conjugate, after deprotection of the thiol group(s). Examples of suitable transfer ligands include glucoheptonate, tartrate, DTPA, EDTA, di, tri or poly-alkylphosphonates, pyrophosphate or glycine and its derivatives. Those skilled in the art recognize that any chelating agent capable of complexing with reduced radionuclide and subsequently transferring the reduced radionuclide to pendant sulfhydryl groups are useful in accordance with the present invention (see, for example, Dean, U.S. Pat. No. 5,180,816 and/or Shochat et al., U.S. Pat. No. 5,061,641, the disclosures of each are incorporated by reference herein in their entirety).

The present invention also encompasses an alternative embodiment whereby the thiol-bound radiometal is "capped" with one or more exogenous ligands (see, Shochat et al., supra). These ligands generally are designed to complete the coordination sphere of the ion and to complement the sulfhydryl group(s) already provided by the protein-chelating agent conjugate. A balance must be struck between ligands that bind the ion so tightly that they weaken the sulfur-metal bond(s) to the protein reactive group(s) and reduce the stability of the radiometal label in serum, and those that provide insufficient chelating power so that the ion is easily extracted from the protein by other exogenous ligands in serum or bone marrow, or in organs such as the liver, spleen or kidneys where clearance occurs. Those skilled in the art are capable of striking this balance using known chemical principles, and are capable of designing a suitable exogenous capping ligand.

A kit for use in radiolabeling a protein, e.g., a Fab' or F(ab')$_2$ fragment, or an intact antibody, with Tc-99m, using generator produced pertechnetate, would include about 0.01–10 mg per unit dose of an antibody or antibody fragment that specifically binds an antigen associated with a tumor, an infectious lesion, a microorganism, a myocardial infarction, a clot, atherosclerotic plaque or a normal organ or tissue, and which further is conjugated to a protected tertiary thiol-containing chelating agent to form an antibody-acetyl-t-thiol derivative that is deprotected to form an antibody-t-thiol derivative. The kit also would include about 0.1–50 μg per unit dose of stannous ions. The constituents of the kit are combined just prior to use with about 2–50 mCi of Tc-99m pertechnetate per mg of antibody or antibody fragment. The antibody/antibody fragment-t-thiol derivative and the Sn(II) reducing agent are advantageously combined in a single solution in a vial which can be stored, e.g., in a liquid nitrogen bath, or lyophilized, preferably with added sugar as is well known in the art, prior to addition of the pertechnetate. Variations including addition of conventional reagents of the foregoing kits are well within the routine skill of those skilled in the art.

If the antibody/antibody fragment-acetyl-t-thiol derivative is used, it can be deprotected prior to admixture with the reducing agent, or after admixture. The protected antibody/antibody fragment-acetyl-t-thiol derivative, however, must be deprotected prior to reaction with the radionuclide. Although the deprotecting agent and the radionuclide may be added to the solution simultaneously, the reaction sequence generally is (i) deprotection of the protected antibody/antibody fragment-acetyl-t-thiol derivative and reduction of the radionuclide, and (ii) labeling the conjugate. Advantageously, however, the antibody/antibody fragment-acetyl-t-thiol derivative is deprotected before admixture with the reducing agent and storage in a kit. Upon reading the present specification, those skilled in the art are capable of designing a method and kit using either a protected or deprotected antibody/antibody fragment-acetyl-t-thiol derivative.

The proteins in the kits of the present invention are advantageously frozen or lyophilized, in sterile containers, and under an inert gas atmosphere, advantageously cooled and stored in a liquid nitrogen bath and gently thawed just prior to use. The kits are conveniently supplemented with sterile vials of buffers, saline, syringes, filters, columns and the like auxiliaries to facilitate preparation of injectable preparations ready for use by the clinician or technician.

In a particularly preferred embodiment of the present invention, radiolabeling of a protein is effected by conjugating (N-hydroxysuccinimidyl) N-(3-methyl-3-acylmercapto butyryl) glycinate ("chelating agent") to antibodies (whole or fragments) by reaction of protein with a molar excess of chelating agent at pH 7.5. The number of thiols added to antibodies can be changed by varying the molar excess of chelating agent employed. The protein-chelating agent conjugate then preferably is purified by conventional means and the purified conjugate can be thiol-deprotected as and when necessary, and once thiol-deprotected, the resultant product is immediately formulated with stannous chloride, and stored as a kit as a lyophilizate, in sealed vials, under an argon atmosphere or in vacuo. This kit then is ready for admixture with the radionuclide.

It will be apparent to one of ordinary skill in the art that the radiolabeled proteins, especially antibodies and antibody fragments, prepared according to the method of the invention, will be suitable, and in fact particularly convenient and efficacious, in methods of non-invasive scintigraphic imaging and for radioantibody therapy of tumors and lesions. In particular, a method of imaging a tumor, an infectious lesion, a myocardial infarction, a clot, atherosclerotic plaque, or a normal organ or tissue, wherein a protein, antibody or antibody fragment which specifically binds to an antigen produced by or associated with the tumor, etc;, and radiolabeled with a pharmaceutically inert radioisotope capable of external detection, is parenterally injected into a human patient and, after a sufficient time for the radiolabeled protein, antibody or antibody fragment to localize and for non-target background to clear, the site or sites of accretion of the radiolabeled protein, antibody or antibody fragment are detected by an external imaging camera, it will be an improvement to use as the radiolabeled protein, antibody or antibody fragment a labeled protein, antibody or antibody fragment made according to the method of the present invention. Such radiolabeled protein, antibody or antibody fragment will not clear significantly in the liver, will provide a good tumor to non-tumor ratio and will provide excellent in vivo targeting to tumor.

In addition, in a method of radioantibody therapy of a patient suffering from a tumor or an infectious lesion, wherein a protein, antibody or antibody fragment that specifically binds to an antigen produced by or associated with a tumor or an infectious lesion, and radiolabeled with a therapeutically effective radioisotope, is parenterally injected into a human patient suffering from such tumor or infectious lesion, it will represent an improvement to use as the radiolabeled protein, antibody or antibody fragment a rhenium radiolabeled protein, antibody or antibody fragment made according to the method of the present invention.

Without further elaboration, it is believed that one skilled in the art can, using the preceding description and following examples, utilize the present invention to its fullest extent. The following preferred specific embodiments are, therefore, to be construed as merely illustrative, and not limitative of the remainder of the disclosure in any way whatsoever. In addition, all of the previously mentioned documents in this description are incorporated by reference herein in their entirety.

EXAMPLES

Example 1

Preparation of (N-Hydroxysuccinimidyl) N-(3-methyl-3-acylmercapto butyryl) glycinate A solution of 1.68 g (10 mmol) of glycine t-butyl ester hydrochloride and 1.4 ml of triethylamine in 50 ml of methylene chloride was stirred, and the precipitated triethylammonium chloride was filtered off. The filtrate was diluted to about 100 ml, mixed with 1.4 ml of triethylamine and added dropwise to a solution of dimethylacroyl chloride (10 mmol) in methylene chloride (10 ml), under an inert atmosphere. The reaction mixture was stirred for 18 hours, washed with water (3×10 ml), and brine (10 ml), and dried (anhydrous $Na_2SO_4$). Flash chromatography on silica gel (230–400 mesh) using gradient elution with an ethyl acetate/hexane mixture yielded 1.0 g (50%) of N-(3,3-dimethylacroyl)glycine t-butyl ester as a yellow liquid.

The N-(3,3-dimethylacroyl)glycine t-butyl ester then was dissolved in an excess (5 ml) of thiolacetic acid and heated at reflux (bath temp. 95° C.) for 3 hours. The reaction mixture was cooled, diluted with diethyl ether, washed with 5% aqueous acetic acid, water and brine, and then dried (anhydrous $Na_2SO_4$). Evaporation of the solvents yielded a residue which was stirred with 10 ml of trifluoroacetic acid (TFA) for 2 hours. Evaporation of the TFA gave a residue which was purified by flash chromatography (silica gel, 230–400 mesh; methanol/methylene chloride gradient). The product (a yellow waxy solid), N-(3-acetylmercapto-3-methylbutyryl)glycine, was characterized by IR and proton-NMR spectra. The proton NMR spectrum (400 mHz; $CDCl_3$) showed signals at 1.52 (s, 6H), 2.26 (s, 3H), 2.87 (s, 2H), 4.06 (d, 2H, J=5.6) and 6.42 (s br., 1H).

The yellow waxy solid product obtained above (363 mg) was dissolved in 10 ml of methylene chloride, and treated with N-hydroxysuccinimide (180 mg; 1 equivalent) and dicyclohexylcarbodiimide (322 mg; 1 equivalent). The reaction mixture was stirred for 18 hours under argon. The precipitated dicyclohexylurea was filtered off, and the filtrate was concentrated. The residue was crystallized from isopropanol to obtain (N-hydroxysuccinimidyl) N-(3-methyl-3-acylmercapto butyryl) glycinate as an off-white solid (yield, 335 mg).

Example 2

Conjugation of (N-Hydroxysuccinimidyl) N-(3-methyl-3-acylmercapto butyryl) glycinate to murine F(ab)$_2$ A solution of a conventionally prepared monoclonal murine antibody to CEA, Immu-14 F(ab)$_2$ (885 μl; 6.26 mg), prepared from IgG purified from ascites, and papain digested in the absence of cysteine, in 50 mM hepes/150 mM saline (pH 7.5) was mixed by vortex with 25 μl of DMF. To this solution, 11 μl of a DMF solution of (N-Hydroxysuccinimidyl) N-(3-methyl-3-acylmercapto butyryl) glycinate (2.3 mg in 345 μl DMF; chelating agent/antibody molar ratio of 4) were added, with mixing by vortex. The resultant clear solution was maintained at 4° C. for 18 hours, or at room temperature for 2 hours to produce an antibody-chelating agent conjugate. The conjugate was purified by centrifuged size-exclusion chromatography on sephadex 50/80 in 0.1 M sodium phosphate and at pH 7. This material was stored in a refrigerator, and thiol-deprotected (example below) as and when required.

Example 3

Thiol-deprotection of the conjugate

One hundred microliters (100 μl) of the conjugate, prepared as described above in Example 2, were mixed with 20 μl of 1 M aqueous hydroxylamine (pH 8) in a 0.6 ml eppendorf vial, mixed by vortex, and purged with argon for 1 minute. After 10 minutes standing at room temperature, the product was purified on a size-exclusion column (sephadex 50/80, 50 mM acetate/150 mM saline, pH 5.3). The eluate was analyzed for concentration and free thiol content. Ellman's assay, using 10 mM 5,5-dithiobis-(2-nitrobenzoic acid) (DTNB) in 0.1 M PBS, pH 7, gave a value of 1.1 thiol groups/antibody which indicates an average of 1.1 equivalents of (N-hydroxysuccinimidyl) N-(3-methyl-3-acylmercapto butyryl) glycinate per antibody.

The conjugation reaction was repeated using six equivalents of (N-hydroxysuccinimidyl) N-(3-methyl-3-acylmercapto butyryl) glycinate to obtain a conjugate with an average of 1.8 to 2.2 thiol groups per antibody.

Example 4

Formulation, lyophilization and technetium-99m labeling of the thiol-deprotected conjugate of Example 3

Freshly thiol-deprotected F(ab')$_2$ conjugate (200 μg, 1.1 thiol per antibody) prepared in accordance with Example 3 was mixed with a solution of 25 μg of tin(II) in 150 μl of tartrate (9.2 mM)-acetate (50 mM)-saline (150 mM)-buffer, and lyophilized in a 2 ml glass vial. The lyophilizate was stored under vacuum in a sealed vial.

Tc-99m radiolabeling was performed by adding 1 ml of (Tc-99m)pertechnetate generator-eluate to achieve a specific activity of 5 mCi/mg. The labeling was performed on the antibody-chelating agent conjugate both with and without lyophilization. Radio-HPLC analysis conducted about 30 minutes post-labeling revealed 100% incorporation of radioactivity into the antibody-chelating agent conjugate. Similar labeling of the lyophilizate showed an incorporation of 97%.

Example 5

Biodistribution of Tc-99m labeled Immu-14 F(ab)$_2$ in nude mice bearing the human colon tumor xenograft LS174T Freshly thiol-deprotected antibody-chelating agent conjugate (200 μg, 1.89 thiol groups per antibody) was labeled with 2 mCi of Tc-99m glucoheptonate in a total volume of 1 ml. HPLC analyses performed on the radiolabeled material, as well as on the antibody-antigen complex formed by a short incubation of the radiolabeled fragment with CEA, revealed the product to be satisfactory in terms of radiochemical purity and immunoreactivity.

The labeled conjugate was administered intravenously to ten LS-174T tumor-bearing female nude mice at 11 weeks of age. Five mice were sacrificed at 4 hours and 24 hours, respectively, post-injection. Organs were excised, and the percent injected dose per gram of tissue, the percent injected dose per organ, and the tumor-to-non-target organ ratios were obtained. The tumor uptake was 4.2 and 4.4% ID/g at 4 hours and 24 hours, respectively. The tumor-to-blood ratio rose from 1.2 at 4 hours to 9.4 at 24 hours. These results indicate retention of in vivo targeting capability, faster clearance than whole IgG and similar tumor-to-blood ratios to Tc-Fab'.

Example 6

Preparation of the conjugate of humanized Immu-14 F(ab')$_2$, and Tc-99m labeling A solution of 2.12 mg (5.5 mg/ml) of a conventionally prepared human monoclonal antibody to CEA, humanized Immu-14 F(ab')$_2$ in 50 mM hepes/150 mM saline buffer (pH 7.5) was incubated with a 6-fold excess of (N-hydroxysuccinimidyl) N-(3-methyl-3-acylmercapto butyryl) glycinate for 2 hours at 30° C. DMF (5% v/v) was used as co-solvent. Purification by centrifuged-size-exclusion chromatography (sephadex 50/80 equilibrated in 0.1 M sodium phosphate, pH 7) yielded a pure conjugate which was thiol-deprotected with 0.16 M (final concentration) of aqueous hydroxylamine (pH 8) for 10 minutes at room temperature. Two successive purifications (on sephadex 50/80, 0.1 M sodium acetate, pH 6.5) provided the thiol-deprotected conjugate which was purged thoroughly with argon, and stored on ice. Ellman's assay for thiols using 10 mM DTNB furnished a value of 2.2 thiol groups per antibody molecule.

Approximately 200 μg of the conjugate prepared above, buffered further with one-tenth of its volume of sodium acetate at pH 6, was mixed with 1 mCi of Tc-99m glucoheptonate (freshly prepared as set forth above). Analysis by radio-HPLC after 20 minutes post-labeling, revealed >95% of radioactivity associated with the humanized antibody, of which only 5.5% was in the form of higher molecular weight material.

The invention has been described by reference to particularly preferred embodiments described above. Those skilled in the art recognize that various modifications can be made to the present invention without significantly departing from the spirit and scope thereof.

What is claimed is:

1. A method of radiolabeling a protein comprising contacting a conjugate of said protein with a radiometal cation that binds sulfhydryl groups,
    wherein said protein conjugate comprises a chelating agent covalently linked to said protein, and
    wherein said chelating agent comprises an N-(3-methyl-3-mercaptobutyryl) glycinate moiety.

2. The method of claim 1, wherein said protein is a whole antibody or an antigen-binding antibody fragment.

3. The method of claim 2, wherein said antigen-binding antibody fragment is a F(ab')$_2$ or F(ab)$_2$.

4. The method of claim 1, wherein said protein comprises a disulfide bond.

5. The method of claim 1, wherein said protein is selected from the group consisting of albumin, drugs, cytokines, enzymes, hormones, immune modulators, and receptors.

6. A radiolabeled protein labeled by the method according to claim 1.

7. The method of claim 1, wherein said chelating agent is covalently linked to said protein via a peptide linker.

8. The method of claim 7, wherein said peptide linker is selected from the group consisting of diglycine and triglycine.

9. The method of claim 1, wherein said N-(3-methyl-3-mercaptobutyryl) glycinate moiety is prepared by deprotection of an N-(3-methyl-3-acylmercaptobutyryl) glycinate moiety.

10. The method of claim 9, wherein said acyl group is an acetyl group.

11. The method of claim 9, wherein said deprotection is carried out using hydroxylamine.

12. The method of claim 1, wherein said chelating agent is covalently linked to said protein by an amide linkage.

13. The method of claim 1, wherein said chelating agent is covalently linked to a carbohydrate group on said protein.

14. The method of claim 1, wherein said protein is labeled with a radiometal cation selected from the group consisting of Cu-67, Hg-197, Pb-203, Ag-111, and Bi-212.

15. A radiolabeled protein labeled by the method according to claim 14.

16. In a method of radioimmunoimaging a tumor, an infectious lesion, a myocardial infarction, a clot, atherosclerotic plaque, or a normal organ or tissue, wherein a protein that specifically binds to an antigen produced by or associated with said tumor, infectious lesion, myocardial infarction, clot, atherosclerotic plaque, or normal organ or tissue, and radiolabeled with a pharmaceutically inert radioisotope, is parenterally injected into a human patient and, after a sufficient time for the radiolabeled protein to localize and for non-target background to clear, the site or sites of accretion of the radiolabeled protein are detected by an external imaging camera,
    wherein said radioisotope is selected from the group consisting of Cu-67, Hg-197, Pb-203, Ag-111, and Bi-212,
    and the improvement wherein said radiolabeled protein is made in accordance with the method of claim 1.

17. The method of claim 16, wherein said protein is a F(ab')$_2$ or F(ab)$_2$ antibody fragment.

18. A method of radioimmunotherapy comprising: parenterally administering to a patient suffering from a tumor or infectious lesion a protein conjugate labeled with a therapeutic isotope, wherein said protein conjugate comprises a chelating agent covalently linked to a protein that binds specifically to said tumor or infectious lesion, wherein said chelating agent comprises an N-(3-methyl-3-mercaptobutyryl) glycinate moiety, and wherein said protein is a whole antibody or an antigen-binding antibody fragment,
    wherein said therapeutic isotope is selected from the group consisting of Cu-67, Hg-197, Pb-203, Ag-111, and Bi-212.

19. The method of claim 18, wherein said protein is a F(ab')$_2$ or F(ab)$_2$ antibody fragment.

* * * * *